United States Patent [19]

Debourge et al.

[11] Patent Number: 4,515,807
[45] Date of Patent: May 7, 1985

[54] THIOGLYCINE DERIVATIVES AND USE AS FUNGICIDES

[75] Inventors: Jean-Claude Debourge, Champagne au Mont d'Or; Guy Lacroix, Lyons, both of France

[73] Assignee: Rhone-Poulenc Agrochimie, Lyons, France

[21] Appl. No.: 427,304

[22] Filed: Sep. 29, 1982

[30] Foreign Application Priority Data

Oct. 6, 1981 [FR] France .............................. 81 18915

[51] Int. Cl.³ .................. C07C 153/023; A01N 37/14
[52] U.S. Cl. ............................. 514/513; 260/455 R; 260/502.6; 549/487
[58] Field of Search ................. 260/455 R, 502.6; 424/301, 317

[56] References Cited

U.S. PATENT DOCUMENTS 4,248,886 2/1981 Lunkenheimer et al. ...... 260/455 R

FOREIGN PATENT DOCUMENTS

| 0045049 | 7/1980 | Fed. Rep. of Germany ... 260/455 R |
| 2176075 | 10/1973 | France ............................ 260/455 R |
| 2267042 | 7/1975 | France ............................ 260/455 R |
| 2326416 | 4/1977 | France ............................ 260/455 R |

OTHER PUBLICATIONS

Noller, Textbook of Organic Chemistry, 2nd Ed., W. B. Saunders, Co., Philadelphia, 1958, p. 185.

Primary Examiner—Henry R. Jiles
Assistant Examiner—Robert C. Whittenbaugh
Attorney, Agent, or Firm—Burns, Doane, Swecker & Mathis

[57] ABSTRACT

Fungicides of the formula:

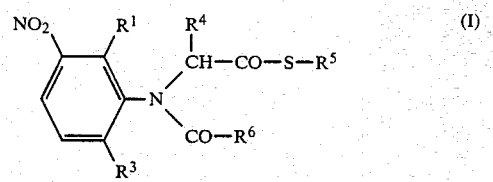

in which:
$R^1$ and $R^3$, which are identical or different, represent an alkyl radical having from 1 to 4 carbon atoms and are preferably the methyl radical,
$R^4$ represents the hydrogen atom or a methyl radical,
$R^5$ represents the hydrogen atom or an alkyl radical having from 1 to 4 carbon atoms,
$R^6$ represents an optionally monohalogenated or dihalogenated alkyl radical having from 1 to 6 carbon atoms, a cycloalkyl radical having from 3 to 6 carbon atoms or a radical $-CH_2-X-R^7$,
X represents the oxygen or sulphur atom, and
$R^7$ represents an alkyl radical having from 1 to 4 carbon atoms.

14 Claims, No Drawings

THIOGLYCINE DERIVATIVES AND USE AS FUNGICIDES

The present invention relates to new products containing an amide group, derived from aniline. The invention also relates to the preparation of the said products and their application for the protection of plants, especially against fungi and fungal diseases.

The compounds according to the invention have the formula:

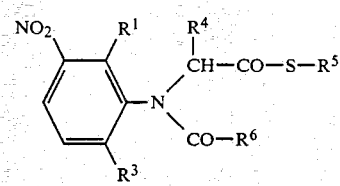

in which:

$R^1$ and $R^3$, which are identical or different, represent an alkyl radical having from 1 to 4 carbon atoms and are preferably the methyl radical, $R^4$ represents the hydrogen atom or a methyl radical, $R^5$ represents the hydrogen atom or an alkyl radical having from 1 to 4 carbon atoms, $R^6$ represents an optionally monohalogenated or dihalogenated alkyl radical having from 1 to 6 carbon atoms, a cycloalkyl radical having from 3 to 6 carbon atoms, a radical $-CH_2-X-R^7$ or a furyl heterocyclic ring, x represents the oxygen or sulphur atom, and $R^7$ represents an alkyl radical having from 1 to 4 carbon atoms.

In the general family of compounds of the formula (I), such as has just been defined, a particular subfamily is especially advantageous; in particular, it exhibits very good antifungal properties, especially with regard to phycomycetes and more particularly with regard to mildews; these preferred products are such that $R^1$, $R^3$, $R^4$ and, if appropriate, $R^7$ represent a methyl group.

In these preferred compounds, the presence of an asymmetric carbon (optical isomerism) in the chain $-CH(R^4)-CO-S-R^5$, on the one hand, and the asymmetry (also called atropisomerism) created by the $NO_2$ substituent on the phenyl nucleus, on the other hand, cause the formation of two stereoisomers (or pseudo-diastereoisomers) which can be observed by various analytical means and can be isolated by physical means. These stereoisomers also form part of the invention.

The compounds according to the invention can be prepared in various ways.

In a first process, a compound of the formula (II) is acylated with an acid chloride of the formula $R^6-CO-Cl$ (III) according to the equation:

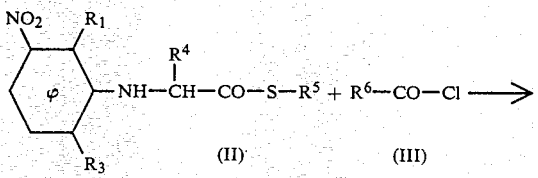

(I) + HCl

The reaction used in this process is advantageously carried out in solution in an inert solvent (i.e. a solvent which does not undergo chemical reaction with the reactants under the operating conditions). The reaction temperature is generally above 40° C. and below the degradation temperature of the reactants and/or reaction products. The temperature is thus generally between 60° and 150° C. In a convenient procedure, the reaction is carried out at the b.p. of the solvent in question. Suitable solvents which may be mentioned are polar or non-polar aprotic organic solvents. It is preferred to use solvents having a b.p. within the range indicated for the reaction temperature; they can therefore be aromatic hydrocarbons (such as benzene, toluene, xylenes and chlorobenzene), aliphatic hydrocarbons (such as hexane, heptane, cyclohexane and methylcyclohexane), chlorinated aliphatic hydrocarbons (such as dichloroethane, dichloroethylene, chloroform and carbon tetrachloride), ethers (such as dioxane, tetrahydrofuran and diethyl ether), ketones (such as acetone, methyl ethyl ketone and methyl isobutyl ketone) or nitriles (such as acetonitrile).

The reaction can be catalysed, e.g. by dimethylformamide; it can be carried out in the absence or presence of a condensation agent, in particular an acid acceptor. Acid acceptors which can be used are tertiary amines such as trialkylamines (e.g. triethylamine), N-aryldialkylamines (e.g. N,N-dimethylaniline) or pyridine and pyridine bases, or inorganic bases such as alkali metal or alkaline earth metal carbonates and hydrogencarbonates, and sodium acetate.

The reaction can be carried out in the presence of an excess of one or other of the reactants. A preferred procedure, however, consists in carrying out the reaction in the presence of an excess of the compound of the formula (II), e.g. by gradually introducing the acid chloride of the formula (III) into the reaction medium containing all or part of the compound of the formula (II) which is to be used, and the reaction is then continued until the evolution of hydrogen chloride has ceased; the amounts of reactants used overall in the course of the reaction are preferably approximately stoichiometric amounts; it is generally most advantageous to use stoichiometric amounts; however, the acid chloride of the formula (II) can be used in excess of the stoichiometric amount, e.g. in an excess of up to 10% (by number). At the end of the reaction, the reaction product of the formula (I) is isolated by any means which is in itself known, e.g. by distillation of the solvent (i.e. evaporation) and/or crystallisation of the product from the medium.

As regards the preparation of the compounds of the formula (II), this can be carried out by similar processes to those described for the preparation of anilinoalkanecarboxylic acid esters in the following publications: J. Org. Chem. 30, pages 4,101–4,104 (1965), and Tetrahedron 1967, pages 487–498.

The acid chlorides of the formula (III) can be prepared according to many known processes, or in a manner similar thereto, but especially the processes described in U.S. Pat. No. 2,412,700, Berichte 46, pages 2,103–2,107 (1913), and Annalen 602, pages 1–14 (1957).

The compounds of the invention can be prepared by a second process, in which an acid of the formula (IV) is esterified with a mercaptan of the formula $R^5SH$ according to the equation:

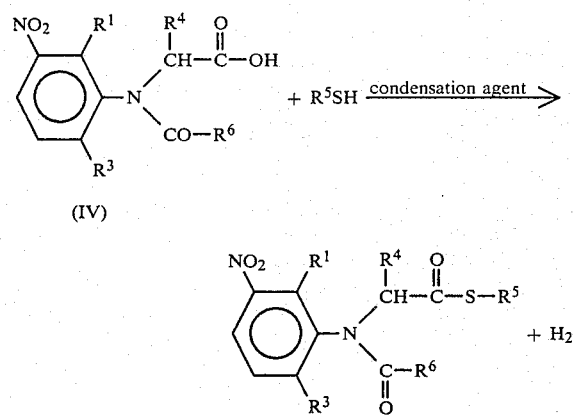

The esterification reaction can be carried out by any of the techniques which are in themselves known.

In particular, it is possible to use a carbodiimide, and more particularly dicyclohexylcarbodiimide, as the dehydrating agent.

In this case, the reaction is most conveniently carried out at temperatures of between 10° and 120° C. in an inert organic solvent. Solvents which may be mentioned are those which can be used in the first process.

Dehydrating agents which may be mentioned are carbodiimides, in particular dicyclohexylcarbodiimide. The amounts of dehydrating agent and acid (IV) are preferably approximately stoichiometric amounts (at least 90% of the stoichiometric amount, relative to the mercaptan of the formula $R^5SH$).

From a practical point of view, it is also preferred to add the carbodiimide gradually to a mixture of mercaptan and acid (IV).

In the course of the reaction, a substituted urea is generally formed, which is removed at the end of the reaction by any means which is in itself known, e.g. by filtration if this substituted urea is insoluble. The solvent is also removed, e.g. by evaporation, which leads to the isolation of the compound of the formula (I).

The acids of the formula (IV) can be prepared by saponification of the compounds of the formula (V):

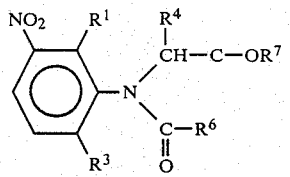

These compounds of the formula (V) can be prepared by the processes described in French Pat. No. 2,267,042.

The examples which follow, which are given without implying a limitation, illustrate the invention and show how it can be put into practice.

Example 1 illustrates the preparation of a compound by the first process.

Example 2 illustrates the preparation of a compound by the second process.

Example 3 illustrates the separation of pseudodiastereoisomers.

The other examples illustrate the application of the products of Examples 1 to 3 and of Table (I).

Solutions of suspensions of active ingredients described in Examples 4 and 5 are sprayed under conditions such that the spraying of a solution or suspension having a concentration of 1 g/liter corresponds on average to the application of about 2 micrograms of active ingredient per $cm^2$ of plant leaf.

Under the conditions of Examples 4 and 5, the compounds illustrated did not exhibit phytotoxicity.

In these Examples 4 and 5, it is considered that a product effects total protection against a fungal disease if the protection is at least 95%; the protection is considered to be good if it is at least 80% (but less than 95%), as fairly good if it is at least 70% (but less than 80%) and as average if it is at least 50% (but less than 70%).

EXAMPLE 1

Preparation of methyl N-(2,6-dimethyl-3-nitrophenyl)-N-chloroacetyl-thiolalaninate (Compound No. 6).

Methyl N-(2,6-dimethyl-3-nitrophenyl)-thiolalaninate (5.4 g; 0.02 mol) and chloroacetyl chloride (2.3 g) are dissolved in toluene (50 ml). The reaction medium is heated gradually to the boil under reflux: the evolution of hydrogen chloride is then observed. The heating under reflux is maintained until the evolution of hydrogen chloride has ceased, i.e. for 3 hours. The reaction medium is cooled to ambient temperature and then washed with water (3×50 ml). The final solution is dried and then concentrated. The residual oil is crystallised from a hexane/ether mixture. The crystals are dispersed in the solvent and then filtered off and dried in vacuo.

This gives a beige solid (6 g) melting at 113° C.

EXAMPLE 2

Preparation of methyl N-(2,6-dimethyl-3-nitrophenyl)-N-methoxyacetyl-thiolglycinate (Compound No. 11).

N-(2,6-Dimethyl-3-nitrophenyl)-N-methoxyacetylglycine of the formula:

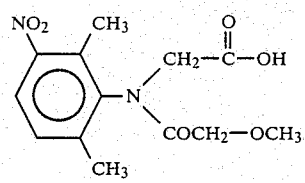

and methylmercaptan ($CH_3{}^{SH}$) (1.1 g) are dissolved in acetonitrile (80 cc).

The solution is stirred at 20° C. and a solution of dicyclohexylcarbodiimide (4.5 g) in acetonitrile (20 cc) is added rapidly.

The reaction medium is heated in an autoclave for 2 hours at 80° C. and then cooled to ambient temperature. The precipitate of dicyclohexylurea is filtered off, the solvent is removed by distillation and methylene chloride (200 ml) is added. The methylene chloride solution is washed with a solution of sodium bicarbonate and then with water. After distillation of the solvent, the residue is taken up in either (20 ml): a beige solid crystallises. The product is filtered off and then dried in vacuo.

This gives a light beige powder (4.5 g). After purification by chromatography on a silica column, a product melting at 102° C. is obtained.

EXAMPLE 3

Separation of the pseudo-diastereoisomers of methyl N-(2,6-dimethyl-3-nitrophenyl)-N-methoxyacetyl-thiolalaninate (Compounds Nos. 1 and 2).

The synthesis of the abovementioned compound is carried out by the first process described; this gives an equimolar mixture of the two pseudo-diastereoisomers of this compound.

Chromatography on a thin layer of silica (MERCK plate: KIESELGEL 60F-254), using a toluene/ethyl acetate mixture in respective proportions by volume of 70/30 as the eluant system, makes it possible to distinguish between the two stereoisomers, the one having an Rf of 0.36 and the other having an Rf of 0.25. Rf denotes the ratio of the final migration height of the compound in question to that of the eluant system. It is also possible to distinguish between these two stereoisomers in NMR spectrography, which indicates that the proportions of these stereoisomers are virtually equal. By convention, the isomer having the higher Rf in the system described above is called isomer A and the one having the lower Rf is called isomer B.

$$Rf(A) > Rf(B)$$

The two isomers are separated by chromatography on a silica column, using the same system as that described above. Each of the isomers crystallises from diethyl ether.

Isomer A is in the form of a pale yellow solid melting at 95.7° C.

Isomer B is also in the form of a pale yellow solid, melting at 139° C.

Compounds Nos. 1 to 11, the characteristics of which are indicated in Table (I) and which have the general formula:

$$O_2N \quad CH_3 \quad R^4$$
$$\varphi - N \begin{cases} CH-CO-S-R^5 \\ CO-R^6 \end{cases}$$
$$CH_3$$

are prepared in a similar manner to that described in these Examples 1 to 3.

EXAMPLE 4

Use in vivo against Plasmopara viticola on vine plants (preventive treatment)

Vine plants (GAMAY variety), cultivated in pots, are treated on both sides of their leaves by being sprayed with an aqueous emulsion containing the active ingredient to be tested; the emulsion sprayed consists of: the active ingredient to be tested (40 mg), water (40 cc) and Tween 80 (surface-active agent consisting of the oleate of an ethylene oxide/sorbitol condensate) (0.02 cc).

This emulsion, made up in this way, makes it possible to spray an aqueous emulsion containing 1 g/liter of active ingredient to be tested. To obtain spraying emulsions in which the concentration of active ingredient to be tested are less than 1 g/liter, the aqueous emulsion made up in this way is diluted with water.

After 48 hours, contamination is carried out by spraying the underside of the leaves with an aqueous suspension of fungus spores (about 80,000 units/cc). The pots are then placed for 48 hours in an incubation cell at 100% relative humidity and at 20° C.

The plants are checked 9 days after infestation.

TABLE (I)

| COMPOUND NO. | $R_4$ | $R_5$ | $R_6$ | ISOMER | M.P. |
|---|---|---|---|---|---|
| 1 | $CH_3-$ | $CH_3-$ | $CH_3OCH_2-$ | Isomer A | 95° C. |
| 2 | $CH_3-$ | $CH_3$ | $CH_3OCH_2-$ | Isomer B | 139° C. |
| 3 | $CH_3-$ | $CH_3-$ | $CH_3SCH_2-$ | Isomer A | 105° C. |
| 4 | $CH_3-$ | $CH_3-$ | $CH_3SCH_2-$ | Isomer B | 117° C. |
| 5 | $CH_3-$ | $CH_3-$ | $CH_3-$ | Mixture of isomers | 108° C. |
| 6 | $CH_3-$ | $CH_3-$ | $ClCH_2-$ | Mixture of isomers | 113° C. |
| 7 | $CH_3-$ | $CH_3-$ | cyclopropyl | Isomer A | 70° C. |
| 8 | $CH_3-$ | $CH_3-$ | cyclopropyl | Isomer B | 153° C. |
| 9 | $CH_3-$ | $CH_3-$ | furyl | Isomer A | 86° C. |
| 10 | $CH_3-$ | $CH_3-$ | furyl | Isomer B | 151° C. |
| 11 | H | $CH_3-$ | $CH_3OCH_2-$ | | 102° C. |

Under these conditions of use, it is observed that:

at a dose of 10 mg/liter, total protection is provided by compounds 6, 7, 8, 9, 10 and 11;

at a dose of 33 mg/liter, total protection is observed for compounds 6, 7 and 9 and good protection for compound 10; and at a dose of 11 mg/liter, compounds 7 and 9 again provide total protection and compounds 6 and 10 provide good protection.

EXAMPLE 5

Use in vivo against "Phytophthora infestans", which is responsible for tomato mildew 60 to 75 day old tomato plants (Marmande variety), cultivated in a greenhouse, are treated by being sprayed with aqueous emulsions prepared as indicated in Example 4 and containing various concentrations of active ingredient to be tested.

After 48 hours, the treated plants are contaminated with an aqueous suspension of spores (zoosporangia) obtained from a culture of "Phytophthora infestans" cultivated for 20 days on a medium based on chick-pea flour.

The tomato plants are placed for 48 hours in an enclosure which is at a temperature of 16° to 18° C. and which is provided with an atmosphere having a relative humidity of 100%, and the relative humidity is then reduced to 80%.

The results are observed 8 days after contamination. The results are assessed by evaluating the surface area of leaves invaded by the fungus and are expressed as the "percentage protection", i.e.

$$100 \left( 1 - \frac{S}{Sc} \right),$$

S being the surface area invaded by the fungus on the plant in question and Sc being the surface area invaded by the fungus on the untreated control plant. As in the previous examples, the results are indicated below in the form of: total, good, fairly good or average protection.

Under these conditions and with an aqueous emulsion in which the concentration of active ingredient to be tested is 33 mg/liter, total protection was observed with compounds nos. 1 and 2 and good protection with compound no. 3.

At a concentration of 11 mg/liter of active ingredient, total protection is observed with the compound of Example 1 and good protection with the compound of Example 2.

At a concentration of 3 mg/liter of active ingredient, total protection is observed with compound no. 1.

EXAMPLE 6

Experiments in vitro on Phythium sp

The compound to be tested is introduced, in the form of an acetone solution (of 1% strength), into a testtube containing a supercooled (60° C.) sterile culture medium. After mixing, the medium containing the product is poured into a Petri dish (diameter: 5 cm) under aseptic conditions. In this way, series of dishes containing doses of active ingredients of 0.3, 1, 3, 10 and 30 mg/liter, respectively, are prepared. After 24 hours, the dishes are inoculated by depositing, at the centre, a mycelium implant (diameter: 8 mm) of the fungus studied.

The growth rate of the fungus on the medium without a product (control) is then compared with the growth rate on the medium containing the doses described above; the growth rate of the fungi is assessed by measuring the diameter of the colony.

The results are graded according to the following scale:
95 to 100% growth inhibition—grade 4
75 to 95% growth inhibition—grade 3
50 to 75% growth inhibition—grade 2
25 to 50% growth inhibition—grade 1
Less than 25% growth inhibition—grade 0.
The results are collated in Table (II).

TABLE (II)

| No. of the compound used | 1 | 2 | 6 | 7 | 9 | 10 |
|---|---|---|---|---|---|---|
| Application dose in mg/l | | | | | | |
| 10 | 4 | 3 | | | | |
| 3 | 4 | 2 | 4 | 4 | 4 | 3 |
| 1 | 4 | 1 | 3 | 3 | 4 | 2 |

These experiments clearly illustrate the noteworthy fungicidal properties of the compounds according to the invention, especially on fungi of the Phycomycetes type, and also their lack of phytotoxicity.

For their use in practice, the compounds according to the invention are rarely employed by themselves. Most frequently, they form part of compositions. These compositions, which can be used for protecting plants against fungal diseases, contain, as the active ingredient, a compound according to the invention such as described above, in association with the solid or liquid carriers which are acceptable in agriculture and the surface-active agents which are also acceptable in agriculture. The customary inert carriers and the customary surface-active agents can be used in particular.

These compositions can also contain all kinds of other ingredients, such as e.g. protective colloids, adhesives, thickeners, thixotropic agents, penetrating agents, stabilisers, sequestering agents and the like, together with other known active ingredients having pesticidal properties (in particular insecticides or fungicides), properties which promote plant growth (in particular fertilisers) or properties which regulate plant growth. More generally, the compounds according to the invention can be used in association with all the solid or liquid additives corresponding to the usual formulation techniques.

The use doses of the compounds according to the invention can vary within wide limits, depending in particular on the virulence of the fungi and on the climatic conditions.

In general, compositions containing 0.5 to 5,000 ppm of active substance are suitable; these values are indicated for the compositions ready for application. Ppm denotes "parts per million". The range of 0.5 to 5,000 ppm corresponds to a range of $5 \times 10^{-5}$ to 0.5% (percentages by weight).

As regards the compositions suitable for storage and transportation, these more advantageously contain from 4 to 95% (by weight) of active substance.

Therefore, the compositions for agricultural use according to the invention can contain the active ingredients according to the invention within very wide limits, ranging from $5.10^{-5}\%$ to 95% (by weight).

According to what has already been stated, the compounds according to the invention are generally used in association with carriers and, if appropriate, surface-active agents.

In the present account, the term "carrier" denotes an organic or inorganic, natural or synthetic material with which the active ingredient is associated in order to facilitate its application to the plant, to seeds or to the soil. This carrier is therefore generally inert and it must be acceptable in agriculture, in particular on the plant treated. The carrier can be solid (clays, natural or synthetic silicates, silica, resins, waxes, solid fertilisers or the like) or liquid (water, alcohols, ketones, petroleum fractions, aromatic or paraffinic hydrocarbons, chlorohydrocarbons, liquefied gases or the like).

The surface-active agent can be an emulsifying, dispersing or wetting agent of the ionic or non-ionic type. Examples which may be mentioned are salts of polyacrylic acids, salts of lignosulphonic acids, salts of phenolsulphonic or naphthalenesulphonic acids, condensates of ethylene oxide with fatty alcohols, fatty acids or fatty amines, substituted phenols (in particular alkylphenols or arylphenols), salts of sulphosuccinic acid esters, taurine derivatives (in particular alkyl-taurates) and phosphoric acid esters of condensates of ethylene oxide with alcohols or phenols. The presence of at least one surface-active agent is generally essential if the active ingredient and/or the inert carrier are not soluble in water and if the vehicle of application is water.

For their application, the compounds of the formula (I) are therefore generally in the form of compositions; these compositions according to the invention are themselves in a fairly wide variety of solid or liquid forms.

As forms of solid compositions, there may be mentioned dusting powders or sprinkling powders (in which the content of compound of the formula (I) can range up to 100%) and granules, in particular those obtained by extrusion, by compaction, by the impregnation of a granular carrier or by the formation of granules from a powder (the content of compound of the formula (I) in these granules being between 1 and 80% for these last cases).

As forms of liquid compositions or compositions which are to be made up into liquid compositions on application, there may be mentioned solutions, in particular water-soluble concentrates, emulsifiable concentrates, emulsions, suspension concentrates, aerosols, wettable powders (or spraying powders) and pastes.

The emulsifiable or soluble concentrates most frequently comprise 10 to 80% of active ingredient, and the emulsions or solutions ready for application contain 0.001 to 20% of active ingredient. In addition to the solvent, and where necessary, the emulsifiable concentrates can contain 2 to 20% of suitable additives such as stabilisers, surface-active agents, penetrating agents, corrosion inhibitors, dyestuffs and adhesives. The compositions of a few concentrates are now given as examples:

| active ingredient | 400 g/liter |
| --- | --- |
| alkali metal dodecylbenzenesulphonate | 24 g/liter |
| 10:1 ethylene oxide/nonylphenol condensate | 16 g/liter |
| cyclohexanone | 200 g/liter |
| aromatic solvent q.s. | 1 liter |

Another formulation of an emulsifiable concentrate uses the following constituents:

| active ingredient | 250 g |
| --- | --- |
| epoxidised vegetable oil | 25 g |
| mixture of an alkylarylsulphonate and a polyglycol ether of fatty alcohols | 100 g |
| dimethylformamide | 50 g |
| xylene | 575 g |

Starting from these concentrates, emulsions of any desired concentration, which are particularly suitable for application to the leaves, can be obtained by dilution with water.

The suspension concentrates, which can also be applied by spraying, are prepared so as to give a stable fluid product which does not form a deposit, and they usually contain from 10 to 75% of active ingredient, from 0.5 to 15% of surface-active agents, from 0.1 to 10% of thixotropic agents, from 0 to 10% of suitable additives such as anti-foam agents, corrosion inhibitors, stabilisers, penetrating agents and adhesives, and, as the carrier, water or an organic liquid in which the active ingredient is sparingly soluble or insoluble; certain organic solids, or inorganic salts, can be dissolved in the carrier in order to assist in preventing sedimentation or to act as anti-freeze agents for the water.

The wettable powders (or spraying powders) are usually prepared so as to contain 20 to 95% of active ingredient, and they usually contain, in addition to the solid carrier, from 0 to 5% of a wetting agent, from 3 to 10% of a dispersing agent and, where necessary, from 0 to 10% of one or more stabilisers and/or other additives such as penetrating agents, adhesives, anti-caking agents, dyestuffs and the like.

Various compositions of wettable powders are now given as examples:

| active ingredient | 50% |
| --- | --- |
| calcium lignosulphonate (deflocculant) | 5% |
| isopropylnaphthalenesulphonate (anionic wetting agent) | 1% |
| anti-caking silica | 5% |
| kaolin (filler) | 39% |

Another composition of a spraying powder, this time of 70% strength, uses the following constituents:

| active ingredient | 700 g |
| --- | --- |
| sodium dibutylnaphthylsulphonate | 50 g |
| 3/2/1 naphthalenesulphonic acid/ phenolsulphonic acid/formaldehyde condensate | 30 g |
| kaolin | 100 g |
| Champagne chalk | 120 g |

Another composition of a spraying powder, this time of 40% strength, uses the following constituents:

| active ingredient | 400 g |
| --- | --- |
| sodium lignosulphonate | 50 g |
| sodium dibutylnaphthalenesulphonate | 10 g |
| silica | 540 g |

Another composition of a spraying powder, this time of 25% strength, uses the following constituents:

| active ingredient | 250 g |
| --- | --- |
| calcium lignosulphonate | 45 g |
| mixture of equal parts by weight of Champagne chalk and hydroxyethylcellulose | 19 g |
| sodium dibutylnaphthalenesulphonate | 15 g |
| silica | 195 g |
| Champagne chalk | 195 g |
| kaolin | 281 g |

Another composition of a 25% strength spraying powder uses the following constituents:

| active ingredient | 250 g |
| --- | --- |
| isooctylphenoxy-polyoxyethylene-ethanol | 25 g |
| mixture of equal parts by weight of Champagne chalk and hydroxyethylcellulose | 17 g |
| sodium aluminosilicate | 543 g |
| kieselguhr | 165 g |

Another composition of a spraying powder, this time of 10% strength, uses the following constituents:

| active ingredient | 100 g |
| --- | --- |
| mixture of sodium salts of saturated fatty acid sulphates | 30 g |
| naphthalenesulphonic acid/formaldehyde condensate | 50 g |
| kaolin | 820 g |

To obtain these spraying powders or wettable powders, the active ingredients are intimately mixed with the additional substances in suitable mixers, and the mixture is ground in mills or other suitable grinders. This gives spraying powders of advantageous wettability and suspendability; they can be suspended in water at any desired concentration, and this suspension can be used very advantageously, in particular for application to the leaves of the plants.

In place of the wettable powders, it is possible to produce pastes. The conditions and modes of production and use of these pastes are similar to those of the wettable powders or spraying powders.

As already stated, the aqueous dispersions and aqueous emulsions, e.g. compositions obtained by diluting, with water, a wettable powder or an emulsifiable concentrate according to the invention, are included in the general scope of the present invention. The emulsions can be of the water-in-oil or oil-in-water type and they can have a thick consistency such as that of a "mayonnaise".

The granules, which are intended to be placed on the soil, are usually prepared so as to have dimensions of between 0.1 and 2 mm, and they can be manufactured by agglomeration or impregnation. In general, the granules contain 0.5 to 25% of active ingredient and 0 to 10% of additives such as stabilisers, slow-release modifiers, binders and solvents.

One example of the composition of granules uses the following constituents:

| active ingredient | 50 g |
|---|---|
| epichlorohydrin | 2.5 g |
| cetyl polyglycol ether | 2.5 g |
| polyethylene glycol | 35 g |
| kaolin (particle size: 0.3 to 0.8 mm) | 910 g |

In this particular case, the active ingredient is mixed with the epichlorohydrin and the mixture is dissolved in acetone (60 g); the polyethylene glycol and the cetyl polyglycol ether are then added. The kaolin is sprayed with the resulting solution and the acetone is then evaporated off in vacuo. Microgranules of this type are advantageously used for combating fungi in the soil.

The compounds of the formula (I) can also be used in the form of dusting powders; it is also possible to use a composition comprising the active ingredient (50 g) and talc (950 g); it is also possible to use a composition comprising the active ingredient (20 g), finely divided silica (10 g) and talc (970 g); these constituents are mixed and ground and the mixture is applied by dusting.

We claim:

1. A product of the formula:

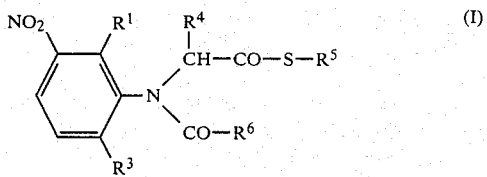

(I)

in which:

$R^1$ and $R^3$, which are identical or different, represent an alkyl radical having from 1 to 4 carbon atoms and are preferably the methyl radical, $R^4$ represents the hydrogen atom or a methyl radical, $R^5$ represents the hydrogen atom or an alkyl radical having from 1 to 4 carbon atoms, $R^6$ represents an optionally monohalogenated or dihalogenated alkyl radical having from 1 to 6 carbon atoms, a cycloalkyl radical having from 3 to 6 carbon atoms or a radical $-CH_2-X-R^7$, X represents the oxygen or sulphur atom, and $R^7$ represents an alkyl radical having from 1 to 4 carbon atoms.

2. A product according to claim 1, in which $R^1$, $R^3$, $R^4$ and, if appropriate, $R^7$ are the methyl group.

3. A product according to one of claims 1 or 2, in which $R^6$ is the group $-CH_2-X-R^7$.

4. A product according to claim 1, which is in the form of a stereoisomer or diastereoisomer.

5. A product according to claim 2, which is in the form of a stereoisomer or diastereoisomer.

6. A product according to claim 3, which is in the form of a stereoisomer or diastereoisomer.

7. A composition which is useful in protecting plants against fungal diseases, which composition comprises a fungicidally effective amount of a compound of claim 1 as the active ingredient, in association with an agriculturally acceptable inert carrier, surface-active agent or mixture thereof.

8. A composition which is useful in protecting plants against fungal diseases, which composition comprises a fungicidally effective amount of a compound of claim 2 as the active ingredient, in association with an agriculturally acceptable inert carrier, surface-active agent or mixture thereof.

9. A composition which is useful in protecting plants against fungal diseases, which composition comprises a fungicidally effective amount of a compound of claim 3 as the active ingredient, in association with an agriculturally acceptable inert carrier, surface-active agent or mixture thereof.

10. A composition according to claim 7, which comprises from $5 \times 10^{-5}$ to 95% active ingredient.

11. A composition according to claim 8, which comprises from $5 \times 10^{-5}$ to 95% active ingredient.

12. A composition according to claim 9, which comprises from $5 \times 10^{-5}$ to 95% active ingredient.

13. A process for combating fungal diseases in plants, which comprises applying to the plant a fungicidally effective amount of the composition of claim 7.

14. A process for combating fungal diseases in plants, which comprises applying to the plant a fungicidally effective amount of the composition of claim 10.

* * * * *